United States Patent [19]

Hoffman et al.

[11] 4,393,245

[45] Jul. 12, 1983

[54] MUSK-LIKE SCENTS AND THEIR MANUFACTURE

[75] Inventors: Werner Hoffman, Neuhofen; Karl von Fraunberg, Bobenheim; Manfred Baumann, Mannheim, all of Fed. Rep. of Germany

[73] Assignee: BASF Aktiengesellschaft, Fed. Rep. of Germany

[21] Appl. No.: 326,597

[22] Filed: Dec. 2, 1981

Related U.S. Application Data

[63] Continuation of Ser. No. 812,153, Jul. 1, 1977, abandoned.

[30] Foreign Application Priority Data

Jul. 9, 1976 [DE] Fed. Rep. of Germany ....... 2630835

[51] Int. Cl.$^3$ .................. C07C 49/547; C07C 49/307
[52] U.S. Cl. .................................... 568/375; 568/350; 568/361; 568/821; 560/231; 252/522 R
[58] Field of Search ........................................ 568/375

[56] References Cited

U.S. PATENT DOCUMENTS 3,754,036  8/1973  Blumenthal .................... 568/375

OTHER PUBLICATIONS

Karpf et al., Helm. Chim. Acta., vol. 58, pp. 2409–2422, (1975).
Graefe et al., Tetrahedron, vol. 26, pp. 2677–2682, (1970).

Primary Examiner—James H. Reamer
Attorney, Agent, or Firm—Keil & Witherspoon

[57] ABSTRACT

New 1-acyl- and 1-hydroxymethyl-cyclododecanes and -cyclododecenes. The new 1-acyl-cyclododecenes and -cyclododecanes are obtained by a Rupe or Meyer-Schuster rearrangement, with or without subsequent hydrogenation in the presence of Ni, Pd and Pt catalysts. The 1-acyl-cyclododecenes and -cyclododecanes are valuable scents of the basic type of the sought-after macrocyclic musk scents. Furthermore, they are used for the manufacture of numerous other new 1-substituted or 1-and 2-substituted cyclododecenes and cyclododecanes having good scent characteristics.

1 Claim, No Drawings

MUSK-LIKE SCENTS AND THEIR MANUFACTURE

This is a continuation of application Ser. No. 812,153 filed July 1, 1977, now abandoned.

The present invention relates to new 1-acyl- and 1-hydroxymethyl-cyclododecanes and -cyclododecenes and to a process for their manufacture.

In particular it relates to cyclododecanes and cyclododecenes of the general formula I

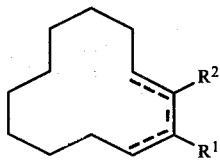

where $R^1$ is H, —$CH_3$ or —$C_2H_5$, preferably H, $R^2$ is —CO—$R^3$ or

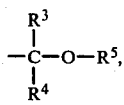

where $R^3$ is alkyl of 1 to 3 carbon atoms, $R^4$ is H or alkyl of 1 to 3 carbon atoms and $R^5$ is H, —COH, —CO—$CH_3$, —CO—$C_2H_5$ or —CO—$C_2H_3$ and in each molecule one or none of the bonds shown in broken lines is an additional bond, ie. cyclododecanes of the general formula I, where $R^1$ to $R^5$ have the above meaning, and their Δ-1,2-, Δ-1,12- or Δ-2,3-dihydrogenation products.

It is an object of the present invention to provide industrially readily accessible, inexpensive compounds which have a scent of the type of the macrocyclic musk scents.

It is well known that macrocyclic musk scents, eg. muscone, cyclopentadecanone, cyclohexadecanone and the like are, because of their olfactory properties, superior to all other conventional musk scents, eg. the tetralin or nitro musk scents.

Since macrocyclic scents are difficult to synthesize and are of limited natural occurrence, they are extremely expensive and their use is restricted to a few luxury articles.

Hence, there is a great demand for compounds which have similar olfactory properties but are cheap.

A musk scent is ascribed to compounds having a disk-like molecular structure; the review by G. Ohloff: "Die Chemie des Geruchssinnes" ("Chemie in unserer Zeit", 5 (1971), 114) alleges that disk-shaped molecules which carry a mobile side chain have a floral type of scent. It was therefore very surprising that the new cyclododecanes and cyclododecenes of the general formula I possess a musk-like type of scent which is very similar to that of the above macrocyclic compounds.

The invention further relates to a process for the manufacture of cyclododecanes and cyclododecenes of the general formula I, as claimed in claim 1, where $R^1$ is H, —$CH_3$ or —$C_2H_5$, $R^2$ is —CO—$CH_3$, —CO—$C_2H_5$ or —CO—$C_3H_7$ and in each molecule one or none of the bonds shown in broken lines is an additional bond, in which process 1-hydroxy-1-alkynyl-cyclododecanes of the general formula II

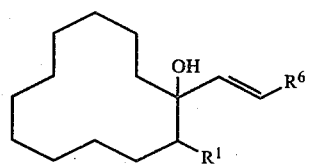

where $R^1$ has the above meaning and $R^6$ is the above radical $R^2$ shortened by —CO—$CH_2$, ie. is —H, —$CH_3$ or —$C_2H_5$, are treated at from −20° to 140° C. with an acid catalyst, the acid strength of which is equal to or greater than that of formic acid and, if none of the bonds shown in broken lines is an additional bond, the resulting cyclododecene is hydrogenated in the presence of Ni, Pd or Pt catalysts.

The 1-hydroxy-1-alkynyl-cyclododecanes of the general formula II required as starting compounds are obtained in the conventional manner by reacting the cyclododecanone, substituted by $R^1$ in the 2-position, with acetylene, propyne or 1-butyne.

Suitable catalysts for the acid-catalyzed rearrangement of the 1-hydroxy-1-alkynyl-cyclododecanes of the general formula II are, in general terms, all acids or acid systems which have an acid strength equal to or greater than that of formic acid, ie. which have a $pK_a$ less than or equal to about 3.77 and which do not attack the starting compound in other ways. Examples are aqueous formic acid or from 70 to 97% strength, aqueous sulfuric acid of various concentrations, sulfuric acid diluted with organic solvents, eg. ethanol, propanol, n-butyl ether and acetic acid, chloroacetic acids, benzenesulfonic acids, strongly acid cation exchangers, such as Dowex 50 in formic acid or acetic acid, anhydrous oxalic acid, HCl in 2-propanol or dry ether, $H_3PO_4$ diluted with acetic acid, p-toluenesulfonic acid, phosphorus pentoxide in benzene, $KHSO_4$, $MgSO_4$ and $NaHSO_4$, especially HCOOH, $H_2SO_4$, HCl and $H_3PO_4$ as such, as mixtures with one another, or diluted with water or organic solvents such as alcohols of 1 to 4 carbon atoms, hydrocarbons or ethers. If cyclododecenes unsaturated in the 1-position are to be manufactured preferentially, the use of mixtures of acetic acid and sulfuric acid (in the ratio of from about 1:1 to 50:1) is particularly advisable. Cyclododecenes unsaturated in the 2-position can be isomerized by treatment with bases, eg. $NaOCH_3$ or $KOC_4H_9$, at from −20° to 100° C., to give the corresponding cyclododecenes unsaturated in the 1-position. Such an isomerization is often advisable for olfactory reasons if a product is (initially) obtained which predominantly contains the isomer unsaturated in the 2-position.

The amount of acid catalyst is not critical. It can be from 0.1 to 10 moles, per mole of acetylene-alcohol. The use of multimolar amounts, ie. the simultaneous use of the catalyst as a solvent, is particularly advisable when using aqueous formic acid.

The reaction times are in general from 15 minutes to 3 hours and the reaction temperature is from −20° to +140° C., preferably from 50° to 120° C.

The two last-mentioned parameters are determined by the nature of the acid catalyst used. The reaction end-point can be determined by, for example, thin layer chromatography.

For further details of these Rupe or Meyer-Schuster rearrangements, reference may be made to S. Swaminathan et al., Chem. Reviews 71 (1971) 5, pages 429–434, and J.Am.Chem.Soc. 75 (1953), 4740.

The process may be carried out batchwise or continuously. The reaction mixture is worked up in the conventional manner, eg. by hydrolysis, extraction with a water-immiscible or only slightly water-miscible inert solvent, and subsequent distillation. The cyclododecenes obtained can be hydrogenated in the presence of supported or unsupported Ni, Pd or Pt catalysts, under atmospheric pressure or superatmospheric pressure, at from 0° to 200° C., preferably from 50° to 100° C. Suitable catalyst carriers are C, SiO$_2$, Al$_2$O$_3$ or CaCO$_3$, especially C. The most advantageous pressure range is from about 0 to 100 bars.

The amounts of catalyst used are in general from 0.1 to 10% by weight. Further details of this catalytic hydrogenation of a double bond are given by G. Schiller in Houben-Weyl, volume IV/2, pages 248–303 (1955) and K. Wimmer in Houben-Weyl, volume IV/2, pages 143–152 and 163–192.

The cyclododecenes of the general formula I, where $R^1$ is H, —CH$_3$ or —C$_2$H$_5$ and $R^2$ is —CO—CH$_3$, —CO—C$_2$H$_5$ or —CO—C$_3$H$_7$ and in each molecule one of the bonds shown in broken lines is an additional bond, which can be manufactured, in accordance with the above process, by acid-catalyzed rearrangement of the 1-hydroxy-1-alkynyl-cyclododecanes of the general formula II, and the cyclododecanes which correspond to the compounds of the formula I and may be obtained from these by hydrogenation, are used to manufacture the remainder of the new compounds of the formula I.

Thus, they can be converted in the conventional manner, by reduction with LiAlH$_4$, NaBH$_4$ or by the Meerwein-Ponndorf method with aluminum isopropylate, to the corresponding cyclododecenes of the general formula I, where $R^2$ is

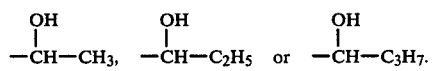

Example 4 describes the reaction of 1-acetyl-1-cyclododecene with NaBH$_4$ to give methyl-1-cyclodecanyl-carbinol as an example of such a reduction.

In addition the cyclododecenes or cyclododecanes can be converted in the conventional manner, by catalytic hydrogenation with metal catalysts eg. Raney nickel and Raney cobalt, to the corresponding cyclododecanes of the general formula I, where $R^2$ is

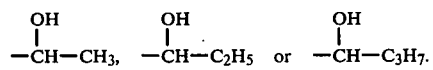

Example 5 describes the conversion of 1-acetyl-1(2)-cyclododecene, in the presence of Raney nickel, to methyl-cyclododecanyl-carbinol, as an example of such a catalytic hydrogenation.

Furthermore, they can be converted, in the conventional manner, by reaction with alkyl-magnesium halides or alkyl-lithium to the corresponding cyclododecenes of the formula I, where $R^2$ is

and $R^3$ and $R^4$ are alkyl of 1 to 3 l carbon atoms. Example 8 describes, as a reaction of this type with organo-metallic compounds, the Grignard reaction of 1-acetyl-1-cyclododecene with methylmagnesium chloride to give dimethyl-cyclododecenyl-carbinol.

The cyclododecanes and cyclododecenes of the formula I which contain an OH group in $R^2$ can be converted, by conventional esterification methods with lower carboxylic acids, their acid chlorides or their anhydrides, to the corresponding carboxylic acid esters, ie. the corresponding compounds of the general formula I, where $R^2$ is

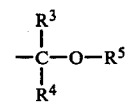

and $R^3$ is alkyl of 1 to 3 carbon atoms, $R^4$ is H or alkyl of 1 to 3 carbon atoms and $R^5$ is —CO—H, —CO—CH$_3$, —CO—C$_2$H$_5$ or —CO—C$_2$H$_3$. In Example 7, the reaction of methyl-cyclododecanyl with glacial acetic acid in the presence of p-toluenesulfonic acid, to give methyl-cyclododecanyl-carbinol acetate, is described as an example of such an esterification.

The new cyclododecanes and cyclododecenes of the general formula I, especially 1-acetyl-1-dodecene and 1-acetyl-dodecane, are valuable scents having the type of odor of the sought-after macrocyclic musk scents. In contrast to the latter, they are relatively easily accessible industrially.

EXAMPLE 1

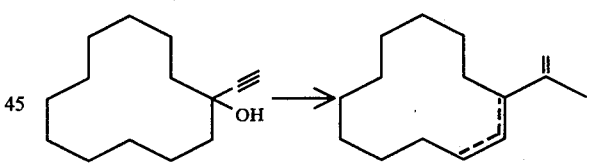

290 g of 1-ethynyl-cyclododecan-1-ol are added, in the course of 30 minutes, to a vigorously stirred mixture of 800 g of concentrated sulfuric acid and 1.5 l of n-hexane. The reaction mixture is then stirred for one hour at −10° C. It is then poured onto about 1 kg of ice and the hexane solution is separated off and washed neutral with sodium bicarbonate solution and water. After distilling off the solvent under reduced pressure at 50° C., 275 g of crude product are left. On subsequent fractional distillation, 234 g of a product of boiling point 90°–95° C./0.1 mm Hg and refractive index $n_D^{25} = 1.5005$ are obtained from the crude product. According to analysis by nuclear magnetic resonance, the product is a 1:1 mixture of 1-acetyl-1-cyclododecene and 1-acetyl-2-cyclododecene. The yield of 1-acetyl-dodecene is accordingly 81% of theory.

Scent: musk-like, earthy, woody, good tenacity.

On treating the product for 60 minutes with catalytic amounts of a solution of sodium methylate in methanol at from 55° C. to 70° C., 1-acetyl-1-cyclododecene of boiling point 87°–90° C./0.005 mm Hg and refractive index $n_D^{25} = 1.5022$ is obtained as the sole product.

EXAMPLE 2

50 g of 1-ethynyl-cyclododecan-1-ol are added to 250 ml of 100% strength acetic acid, in which 10 ml of 98% strength sulfuric acid are dissolved, and the reaction mixture is heated to 60° C. Hereupon, an exothermic reaction occurs and the mixture is cooled to prevent the reaction temperature from rising above 65° C. After completion of the reaction, the solution is stirred for one hour at 60° C. and is then hydrolyzed with 0.5 kg of ice. The product is isolated by extraction with ether, neutralization of the ether phase with sodium bicarbonate solution and water, and distillation. 46 g (corresponding to 91% of theory) of 1-acetyl-1-cyclododecene of boiling point 87°–90° C./0.005 mm Hg and refractive index $n_D^{25} = 1.5022$ are obtained. According to analysis by nuclear magnetic resonance, the product is spectroscopically pure.

EXAMPLE 3

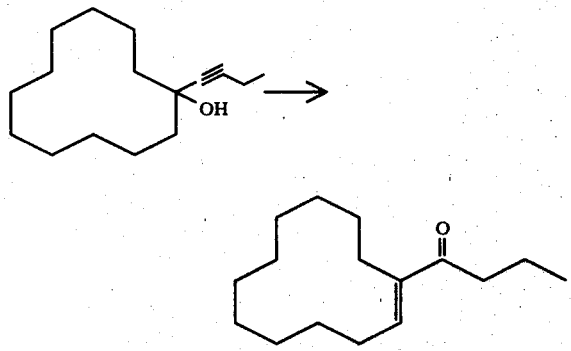

On reacting 50 g of 1-butynyl-cyclododecan-1-ol by the method described in Example 2, 42 g (84% yield) of 1-butyryl-1-cyclododecene are obtained; according to analysis by nuclear magnetic resonance, the product is spectroscopically pure. Boiling point 107°–110° C./0.01 mm Hg, $n_D^{25} = 1.4969$.

Scent: powdery, earthy, slightly musky, woody.

EXAMPLE 4

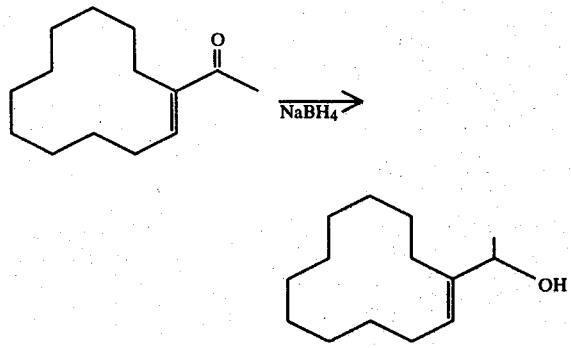

30 g of the 1-acetyl-1-cyclododecene obtained as described in Example 2 are dissolved in 100 ml of ethanol and 3 g of sodium borohydride are added in portions. The reaction temperature is kept at 30° C. by cooling. After a further hour of reaction time at room temperature, the alcohol is distilled off under reduced pressure at 50° C. and the residue is hydrolyzed with ice-cold 2 N sulfuric acid. The methyl-1-cyclododecen-1-yl-carbinol obtained is isolated by extraction with ether, and distillation. Boiling point = 98°–100° C./0.01 mm Hg, $n_D^{25} = 1.5014$; 29 g yield (95% of theory)).

Scent: musky, ambrette, powdery.

EXAMPLE 5

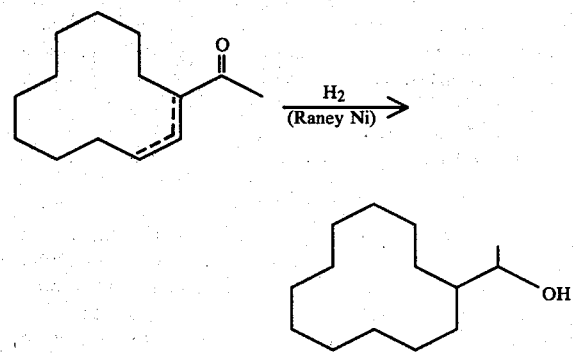

50 g of the 1-acetyl-1(2)-cyclododecene prepared as described in Example 1 are dissolved in 30 ml of ethyl acetate, mixed with 5 g of Raney nickel and hydrogenated at 100° C. and 150 bars hydrogen pressure. When the hydrogen absorption has ceased, the catalyst is filtered off and the methyl-cyclododecanyl-carbinol formed is isolated by distillation.

Boiling point = 110°–114° C./0.05 mm Hg, melting point 35° C.

Scent: musky

EXAMPLE 6

50 g of the 1-acetyl-1-cyclododecene prepared as described in Example 2 are dissolved in 50 ml of ethyl acetate, mixed with 5 g of an 0.5% strength palladium-on-alumina supported catalyst and hydrogenated at 25° C. and 1.5 bars hydrogen pressure.

When the hydrogen absorption has ceased, the catalyst is filtered off and the acetyl-cyclododecane obtained is isolated by distillation. Boiling point = 85°–87° C./0.03 mm Hg; solidification point, after recrystallization from alcohol = 38° C.

Scent: musky, with a somewhat sweet note, good tenacity.

EXAMPLE 7

36 g (0.17 mole) of the methyl-cyclododecanyl-carbinol prepared as described in Example 5 are dissolved in 200 ml of cyclohexane, mixed with 30 g of glacial acetic acid and 0.5 g of p-toluenesulfonic acid and heated to the boil. Water and cyclohexane are distilled off slowly through a 50 cm column with a distillation head. After completion of the elimination of water-which requires about 2 hours-the cyclohexane solution remaining in the reaction vessel is allowed to cool and is then washed neutral with sodium bicarbonate solution, and the cyclohexane is stripped off at 50° C./20 mm Hg.

The crude product which remains is fractionated, giving 39 g of methyl-cyclododecanyl-carbinyl acetate (yield 91%). Boiling point = 110°–112° C./0.01 mm Hg, $n_D^{25} = 1.4780$.

Scent: earthy, musky.

EXAMPLE 8

52 g (0.25 mole) of 1-acetyl-1-cyclododecene, prepared as described in Example 2, are added over 30 minutes to 200 ml of a 1.5-molar solution of methylmagnesium chloride in tetrahydrofuran at from 0° to +10° C. After completion of the addition, the reaction mixture is hydrolyzed with 20 ml of water and the tetrahydrofuran solution is filtered to remove the salt which has precipitated. After destilling off the tetrahydrofuran under reduced pressure (50° C./20 mbars) the product which remains is fractionated. 52 g of dimethyl-cyclododecenyl-carbinol (96% yield) of boiling point=108°-112° C./0.01 mm Hg and refractive index $n_D^{25}=1.5000$ are obtained.

Scent: musky, good tenacity.

EXAMPLE 9

5 g of 1-ethynyl-2-methyl-cyclododecanol are added dropwise over 2 minutes to a solution of 30 ml of glacial acetic acid and 1 ml of concentrated sulfuric acid, whilst stirring at 30° C. The reaction mixture is then stirred for 60 minutes at 60° C., after which it is hydrolyzed with 200 ml of ice water and the product is isolated by extraction with ether and working up in the conventional manner. On distillation, 4.2 g (84% yield) of a yellowish oil of boiling point=86°-90° C./0.1 mm Hg are obtained.

According to NMR analysis, the above product is a mixture of the double bond isomers 1-acetyl-2-methyl-cyclo-1-dodecene, -2-dodecene and -11-dodecene, with the last-mentioned predominating.

Scent: musky, warm woody.

We claim:

1. The compound 1-acetyl-1-cyclododecene having a musk-like scent of the formula

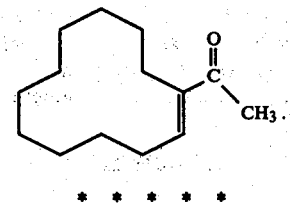

* * * * *